United States Patent [19]

Donovan

[11] Patent Number: 5,196,342
[45] Date of Patent: Mar. 23, 1993

[54] BACILLUS THURINGIENSIS P-2 TOXIN GENE

[75] Inventor: William P. Donovan, Yardley, Pa.

[73] Assignee: PruTech R&D Partnership II, Santa Clara, Calif.

[21] Appl. No.: 630,379

[22] Filed: Dec. 18, 1990

Related U.S. Application Data

[63] Continuation of Ser. No. 39,542, Apr. 16, 1987, abandoned.

[51] Int. Cl.$^5$ .................. C12N 15/32; C12N 15/75
[52] U.S. Cl. ........................ 435/320.1; 435/172.3; 536/23.71
[58] Field of Search ............ 536/27; 435/172.3, 320.1

[56] References Cited

FOREIGN PATENT DOCUMENTS 63949 11/1982 European Pat. Off. .

OTHER PUBLICATIONS

Ziegler et al. Nature vol. 214:404-405 (1967).
Adanz et al. (1985) Gene 36:389-300.
Hames et al. (1985) *Nucleic Acid Hybridization*, IRL Press, Washington, D.C., p. 30.
Old et al. (1981) *Principles of Gene Manipulation*, Univ. of California Press, Berkeley, pp. 104-105 and 119-120.
DM Glover (1984) *Gene Cloning*, Chapman and Hall, London, pp. 102-104.
Kondo et al., "Cloning and Sequencing of Two ...", *Agric. Biol. Chem.* 51, 455-463 (1987).
Brousseau et al., "Bacillus Thuringiensis Crystal Toxins ...", *Biotech. Adv.*, vol. 6, Pergamon Press, pp. 697-724 (1988).
Donovan et al., "Amino Acid Sequence and Entomocidal Activity ...", *J. Biol. Chem.*, 264, 4740 (1989).
Nicholls et al., "Evidence of Two Different Types of P2 Toxins ...", *J. Bact.*, 171, 5141-5147 (1989).
Widner et al., "Two Highly Related Insecticidal Proteins ...", *J. Bact.*, 171, 965-974 (1989).
H',uml/o/ fte et al., "Insecticidal Crystal Proteins ...", *Microbiol. Rev.*, 53, 242-255 (1989).
Yamamoto and McLaughlin, 1981, Biochem. Biophys. Res. Commun. 103:414-421.
Yamamoto and Iizuka, 1983, Arch. Biochem. Biophys. 227:223-241.
Yamamoto, 1983, J. Gen. Microbiol. 129:2595-2603.
Iizuka and Yamamoto, 1983, FEMS Microbiol. Lett. 19:187-192.
Carlton et al., 1985, in The Molecular Biology of the Bacilli (D. Dubnau, ed.) pp. 211-249, Academic Press.
Aronson et al., 1986, Microbiol. Rev. 50:1-24.
Donovan et al., 1988, J. Biol. Chem. 263:561-567.
Whiteley et al., 1986, Ann. Rev. Microbiol. 40:549-576.
Whiteley et al., 1988, in Genetics and Biotechnology of Bacilli, vol. 2, (Ganesan et al., ed.), pp. 239-244, Academic Press.
Wong, et al., 1983, J. Biol. Chem. 258:1960-1967.
Miller et al., 1983, Science 219:715-721.
Schnepf and Whiteley, U.S. Pat. No. 4,448,885, 1984.
Ward et al., 1984, FEBS Lett. 175:377-382.
Schnepf et al., U.S. Pat. No. 4,467,036, 1984.
Waalwijk et al., 1985, Nucl. Acids REs. 13:8207-8217.
Sekar and Carlton, 1985, Gene 33:151-158.
Shibano et al., 1985, Gene 34:243-251.
Adang et al., 1985, Gene 36:289-300.
Whiteley and Schnepf, PCT Application WO 86/01536 (PCT WO 85/01665), 1986.
Wong, et al., 1986, J. Bacteriol. 168:1005-1009.
Barnes et al., U.S. Pat. No. 4,695,455, 1987.
Laemmli and Favre, 1973, J. Mol. Biol. 80:575-599.
Sanger et al., 1977, Proc. Natl. Acad. Sci. U.S.A. 74:5463-5467.
Southern, 1975, J. Mol. Biol. 98:503-517.
Eckhardt, 1978, Plasmid 1:584-588.
Roberts and Lauer, 1979, Methl. Enzym. 68:473-482.
Cohen and Boyer, U.S. Pat. No. 4,237,224, 1980.
Daum, Bulletin of the Entomological Soc. of America, vol. 16 (1), pp. 10-15.

*Primary Examiner*—Richard A. Schwartz
*Assistant Examiner*—John L. LeGuyader
*Attorney, Agent, or Firm*—Christopher Egolf; Alan S. Nadel

[57] ABSTRACT

This invention relates to a crystalline protein toxin useful as a biological insecticide which is known as P-2 toxin, or P-2 delta-endotoxin and which is produced by *Bacillus thuringiensis*. More specifically, this invention relates to the cloning and expression in various microorganisms of the gene coding for the P-2 delta-endotoxin.

12 Claims, 8 Drawing Sheets

```
         AccI  10        20        30        40        50        60
         GTATACACACAAGATTTAATTGATACGTATAATCAAAGTCAGAATTGTGATTGTGGTTGT       FIG. 2
              ____

70        80        90       100       110       120
              AAGTAGTAAGTAGTAAGTAGTTTCTTAAACATACTCGTTATTATCAAAAGAGTTTAGTTT 130       140       150       160       170       180
              TAATATAAAACTAGATATTTAAGGAGGAATTTTATATGAATAATGTATTGAATAGTGGAA
                                                  MetAsnAsnValLeuAsnSerGlyA 190       200       210       220       230       240
              GAACAACTATTTGTGATGCGTATAATGTAGTAGCCCATGATCCATTTAGTTTTGAACATA
              rgThrThrIleCysAspAlaTyrAsnValValAlaHisAspProPheSerPheGluHisL 250       260       270       280       290       300
              AATCATTAGATACCATCCAAAAAGAATGGATGGAGTGGAAAAGAACAGATCATAGTTTAT
              ysSerLeuAspThrIleGlnLysGluTrpMetGluTrpLysArgThrAspHisSerLeuT 310       320       330       340       350       360
              ATGTAGCTCCTGTAGTCGGAACTGTGTCTAGTTTTTTGCTAAAGAAAGTGGGGAGTCTTA
              yrValAlaProValValGlyThrValSerSerPheLeuLeuLysLysValGlySerLeuI 370       380       390       400       410       420
              TTGGAAAAAGGATATTGAGTGAATTATGGGGGATAATATTTCCTAGTGGTAGTACAAATC
              leGlyLysArgIleLeuSerGluLeuTrpGlyIleIlePheProSerGlySerThrAsnL 430       440       450       460       470       480
              TAATGCAAGATATTTTAAGGGAGACAGAACAATTCCTAAATCAAAGACTTAATACAGATA
              euMetGlnAspIleLeuArgGluThrGluGlnPheLeuAsnGlnArgLeuAsnThrAspT 490       500       510       520       530       540
              CCCTTGCTCGTGTAAATGCAGAATTGATAGGGCTCCAAGCGAATATAAGGGAGTTTAATC
              hrLeuAlaArgValAsnAlaGluLeuIleGlyLeuGlnAlaAsnIleArgGluPheAsnG 550       560       570       580       590       600
              AACAAGTAGATAATTTTTTAAACCCTACTCAAAACCCTGTTCCTTTATCAATAACTTCTT
              lnGlnValAspAsnPheLeuAsnProThrGlnAsnProValProLeuSerIleThrSerS 610       620       630       640       650       660
              CGGTTAATACAATGCAGCAATTATTTCTAAATAGATTACCCCAGTTCCAGATACAAGGAT
              erValAsnThrMetGlnGlnLeuPheLeuAsnArgLeuProGlnPheGlnIleGlnGlyT 670       680       690       700       710       720
              ACCAGTTGTTATTATTACCTTTATTTGCACAGGCAGCCAATATGCATCTTTCTTTTATTA
              yrGlnLeuLeuLeuLeuProLeuPheAlaGlnAlaAlaAsnMetHisLeuSerPheIleA 730       740       750       760       770       780
              GAGATGTTATTCTTAATGCAGATGAATGGGGTATTTCAGCAGCAACATTACGTACGTATC
              rgAspValIleLeuAsnAlaAspGluTrpGlyIleSerAlaAlaThrLeuArgThrTyrA 790       800       810       820       830       840
              GAGATTACCTGAGAAATTATACAAGAGATTATTCTAATTATTGTATAAATACGTATCAAA
              rgAspTyrLeuArgAsnTyrThrArgAspTyrSerAsnTyrCysIleAsnThrTyrGlnT 850       860       870       880       890       900
              CTGCGTTTAGAGGGTTAAACACCCGTTTACACGATATGTTAGAATTTAGAACATATATGT
              hrAlaPheArgGlyLeuAsnThrArgLeuHisAspMetLeuGluPheArgThrTyrMetP
``` p2 1'

```
       910       920       930       940       950       960
TTTTAAATGTATTTGAATATGTATCCATTTGGTCATTGTTTAAATATCAGAGTCTTATGG
heLeuAsnValPheGluTyrValSerIleTrpSerLeuPheLysTyrGlnSerLeuMetV 970       980       990      1000      1010      1020
TATCTTCTGGCGCTAATTTATATGCTAGCGGTAGTGGACCACAGCAGACACAATCATTTA
alSerSerGlyAlaAsnLeuTyrAlaSerGlySerGlyProGlnGlnThrGlnSerPheT 1030      1040      1050      1060      1070      1080
CAGCACAAAACTGGCCATTTTTATATTCTCTTTTCCAAGTTAATTCGAATTATATATTAT
hrAlaGlnAsnTrpProPheLeuTyrSerLeuPheGlnValAsnSerAsnTyrIleLeuS 1090      1100      1110      1120      1130      1140
CTGGTATTAGTGGTACTAGGCTTTCTATTACCTTCCCTAATATTGGTGGTTTACCGGGTA
erGlyIleSerGlyThrArgLeuSerIleThrPheProAsnIleGlyGlyLeuProGlyS 1150      1160      1170      1180      1190      1200
GTACTACAACTCATTCATTGAATAGTGCCAGGGTTAATTATAGCGGAGGAGTTTCATCTG
erThrThrThrHisSerLeuAsnSerAlaArgValAsnTyrSerGlyGlyValSerSerG 1210      1220      1230      1240      1250      1260
GTCTCATAGGGGCGACTAATCTCAATCACAACTTTAATTGCAGCACGGTCCTCCCTCCTT
lyLeuIleGlyAlaThrAsnLeuAsnHisAsnPheAsnCysSerThrValLeuProProL 1270      1280      1290      1300      1310      1320
TATCAACACCATTTGTTAGAAGTTGGCTGGATTCAGGTACAGATCGAGAGGGCGTTGCTA
euSerThrProPheValArgSerTrpLeuAspSerGlyThrAspArgGluGlyValAlaT 1330      1340      1350      1360      1370      1380
CCTCTACGAATTGGCAGACAGAATCGTTTCAAACAACTTTAAGTTTAAGGTGTGGTGCTT
hrSerThrAsnTrpGlnThrGluSerPheGlnThrThrLeuSerLeuArgCysGlyAlaP 1390      1400      1410      1420      1430      1440
TTTCAGCCCGTGGAAATTCAAACTATTTCCCAGATTATTTTTATCCGTAATATTTCTGGGG
heSerAlaArgGlyAsnSerAsnTyrPheProAspTyrPheIleArgAsnIleSerGlyV 1450      1460      1470      1480      1490      1500
TTCCTTTAGTTATTAGAAACGAAGATCTAACAAGACCGTTACACTATAACCAAATAAGAA
alProLeuValIleArgAsnGluAspLeuThrArgProLeuHisTyrAsnGlnIleArgA 1510      1520      1530      1540      1550      1560
ATATAGAAAGTCCTTCGGGAACACCTGGTGGAGCACGGGCCTATTTGGTATCTGTGCATA
snIleGluSerProSerGlyThrProGlyGlyAlaArgAlaTyrLeuValSerValHisA 1570      1580      1590      1600      1610      1620
ACAGAAAAAAATAATATCTATGCCGCTAATGAAAATGGTACTATGATCCATTTGGCGCCAG
snArgLysAsnAsnIleTyrAlaAlaAsnGluAsnGlyThrMetIleHisLeuAlaProG 1630      1640      1650      1660      1670      1680
AAGATTATACAGGATTTACTATATCGCCAATACATGCCACTCAAGTGAATAATCAAACTC
luAspTyrThrGlyPheThrIleSerProIleHisAlaThrGlnValAsnAsnGlnThrA 1690      1700      1710      1720      1730      1740
GAACATTTATTTCTGAAAAATTTGGAAATCAAGGTGATTCCTTAAGATTTGAACAAAGCA
rgThrPheIleSerGluLysPheGlyAsnGlnGlyAspSerLeuArgPheGluGlnSerA 1750      1760      1770      1780      1790      1800
ACACGACAGCTCGTTATACGCTTAGAGGGAATGGAAATAGTTACAATCTTTATTTAAGAG
snThrThrAlaArgTyrThrLeuArgGlyAsnGlyAsnSerTyrAsnLeuTyrLeuArgV
```

```
         1810      1820      1830      1840      1850      1860
    TATCTTCAATAGGAAATTCAACTATTCGAGTTACTATAAACGGTAGAGTTTATACTGTTT
    alSerSerIleGlyAsnSerThrIleArgValThrIleAsnGlyArgValTyrThrValS 1870      1880      1890      1900      1910      1920
    CAAATGTTAATACCACTACAAATAACGATGGAGTTAATGATAATGGAGCTCGTTTTTCAG
    erAsnValAsnThrThrThrAsnAsnAspGlyValAsnAspAsnGlyAlaArgPheSerA 1930      1940      1950      1960      1970      1980
    ATATTAATATCGGTAATATAGTAGCAAGTGATAATACTAATGTAACGCTAGATATAAATG
    spIleAsnIleGlyAsnIleValAlaSerAspAsnThrAsnValThrLeuAspIleAsnV 1990      2000      2010      2020      2030      2040
    TGACATTAAACTCCGGTACTCCATTTGATCTCATGAATATTATGTTTGTGCCAACTAATC
    alThrLeuAsnSerGlyThrProPheAspLeuMetAsnIleMetPheValProThrAsnL 2050      2060      2070      2080      2090      2100
    TTCCACCACTTTATTAAGGTTTGAGTGAATGTACAATTAGTATTTTATTCTATCATAAAT
    euProProLeuTyrEnd 2110      2120      2130      2140      2150      2160
    TTAATAGAAAATTCTTAAACATATTGACGGAACTAAATGATATATAATTATGGATATTAG 2170      2180      2190      2200      2210      2220
    AGGGTGTCTTAAAGTAGTAAAATTCTTACTCTGAGACACCCTCTTTATTTTTTTATATCC 2230      2240      2250      2260
    AAATCGGATGAAATATGGGAGAAATCATTTCAAGTTAACCTAAAAGCTT
                                                 Hind III
```

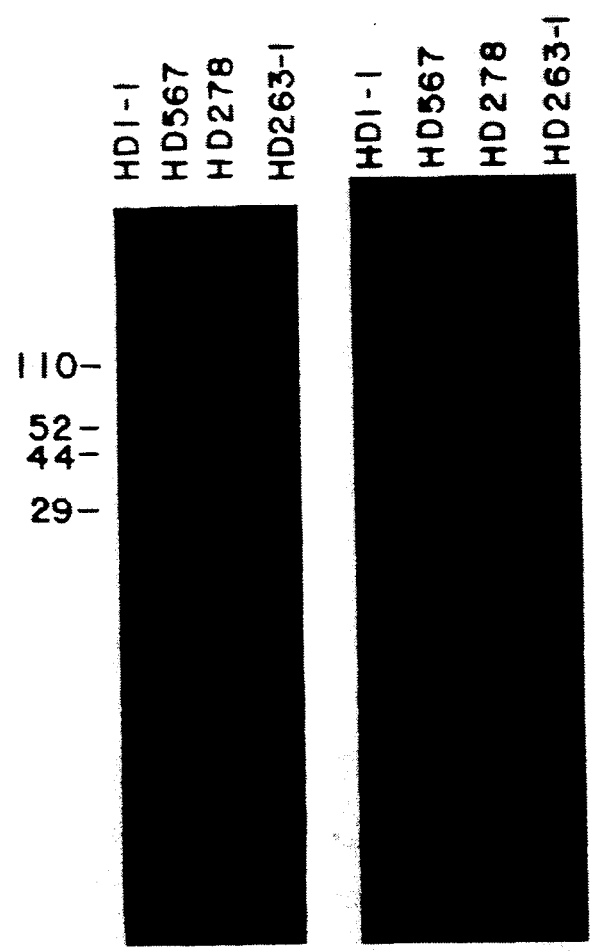

FIG. 6

HOMOLOGY BETWEEN P 2 AND P 1 AMINO ACID SEQUENCES

```
p2 protein
Parasporal crystal protein - Bacillus thuringiensis (fragment)

Amino Acid Number

162   ProGlnPheGlnIleGlnGlyTyrGlnLeuLeuLeuLeuProLeuPheAlaGlnAlaAla   P2
146   ProLeuLeuAlaValGlnAsnTyrGlnValProLeuLeuSerValTyrValGlnAlaAla   P1
         *  *  *  *     *        *  *        *  *  *  *

132   AsnMetHisLeuSerPheIleArgAspValIleLeuAsnAlaAspGluTrpGlyIleSer   P2
166   AsnLeuHisLeuSerValLeuArgAspValSerValPheGlyGlnAngTrpGlyPheAsp   P1
         *           *  *           *  *  *  *  *  *        *  *

2C2   AlaAlaThrLeuArgThr   TyrArgAspTyrLeuArg         AsnTyrThrArg   P2
186   AlaAlaThrIleAsnSerArgTyrAsnAspLeuThrArgLeuIleGlyAsnTyrThr      P1
               *  *  *  *     *     *  *     *  *  *        *

218   AspTyrSerAsnTyrCysIleAsnThrTyrGlnThrAlaPheArgGlyLeuAsnThrArg   P2
205   AspTyrAlaValArgTrpTyrAsnThrGlyLeuGluArgValTrpGlyProAspSerArg   P1
            *  *  *  *  *        *  *  *  *  *  *     *  *  *

238   LeLHisAspMetLeuGlu   PheArgThrTyrMetPheLeuAsnValPheGluTyrVal   P2
225   AspTrpValArgTyrAsnGlnPheArgArgGluLeuThrLeuThrValLeuAspIleVal   P1
      *  *  *  *  *  *  *        *  *  *  *     *     *  *  *

257   SerIleTrpSer     260  P2
245   AlaLeuPheSer     248  P1
      *  *  *

Matches = 39        Length = 104        Matches/length = 37.5 percent
```

BACILLUS THURINGIENSIS P-2 TOXIN GENE

CROSS REFERENCE TO RELATED APPLICATION

This application is a continuation of co-pending U.S. application Ser. No. 39,542, filed Apr. 16, 1987 now abandoned.

INTRODUCTION

This invention relates to a crystalline protein which is useful as a biological insecticide and is known as P-2 toxin, or P-2 delta-endotoxin. It is naturally produced by certain strains of *Bacillus thruingiensis*. More specifically, this invention relates to the cloning and expression in various microorganisms of the gene coding for the P-2 delta-endotoxin, and related novel insecticide compositions incorporating the P-2 toxin itself and microorganisms transformed with the P-2 gene.

BACKGROUND OF THE INVENTION

Commercial Pesticides: General Considerations

Each year, significant portions of the world's commercially important agricultural crops are lost to insects and other pest infestation. The damage wrought by these pests extends to all areas of commercially important plants including foods, textiles, and various domestic plants, and the economic damage runs well into the millions of dollars. Thus, protection of crops from such infestations is of paramount concern.

Broad spectrum pesticides are most commonly used for crop protection, but indiscriminate use of these agents can lead to disruption of the plant's natural defensive agents. Furthermore, because of their broad spectrum of activity, the chemical pesticides may destroy non-target organisms such as beneficial insects and parasites of destructive pests. These are also frequently toxic to animals and humans and, thus, pose environmental hazards when applied.

Additionally, insects and other organisms have frequently developed resistance to these pesticides when repeatedly exposed to them. In addition to reducing the utility of the pesticide, resistant strains of minor pests may become major infestation problems due to the reduction of beneficial parasitic organisms.

This is a major problem encountered in using broad spectrum pesticides. What is needed is a biodegradable pesticide that combines a narrower spectrum of activity with the ability to maintain its activity over an extended period of time, i.e., to which resistance develops much more slowly, or not at all. Biopesticides appear to be useful in this regard.

Biological Pesticides

Biopesticides, also called biorationals, make use of naturally occurring pathogens to control insects, fungal, and weed infestations of agricultural crops. Such substances may comprise a bacterium which produce a substance toxic to the infesting agent (such as a toxin), with or without a bacterial growth medium. Such bacteria can be applied directly to the plants by standard methods of application and will typically persist on the crops for an extended period of time, decreasing the need for repeat applications.

The use of biological methods of pest control was first suggested in 1895 when a fungal disease was discovered in silkworms. It was not until 1940, however, when spores of the milky disease bacterium *Bacillus popilliae* were used to control the Japanese beetle, that successful biological pest control was first achieved. In the late 1960's, the discovery of a new strain of bacterium that secreted a toxin fatal to caterpillars set the stage for commercial biopesticides. The bacterium, named *Bacillus thuringiensis* (hereinafter referred to alternatively as "B.t.") is currently the most widely used biopesticide.

Bacillus Thuringiensis and Delta-Endotoxins

*Bacillus thuringiensis* is a widely distributed, rod shaped, aerobic and spore forming microorganism. During its sporulation cycle B.t. forms proteins known as protoxins or delta-endotoxins. These pathogenecity are deposited in B.t. as parasporal, crystalline inclusions or as part of the spore coat. The patogenicity of B.t. to a variety of sensitive insects, such as those in the Order Lepidoptera and Diptera, is essentially due to this parasporal crystal, which may represent over 20% of the dry weight of the B.t. cell at the time of sporulation.

The parasporal crystal is active in the insect only after ingestion. For instance, after ingestion by a lepidopteran insect, the alkaline pH and proteolytic enzymes in the mid-gut activate the crystal allowing the release of the toxic components. These toxic components poison the mid-gut cells causing the insect to cease feeding and, eventually, to die. In fact, B.t. has proven to be an effective and environmentally safe insecticide in dealing with lepidopteran pests.

It has been reported that different strains of B.t. produce serologically different parasporal crystals. However, one of the predominant crystal forms produced by many of the B.t. strains is a form known as P-1. P-1 has a molecular weight of about 130,000-dalton and it is also thought to be a major component of the spore coat. The genes for the parasporal crystal P-1 and those of most of the other protein crystals, have been discovered to reside on any one of a large number of different plasmids of varying size in B.t.

Delta-Endotoxin Gene Cloning

Since B.t. toxin genes typically reside on plasmids and their products have proven to be effective insecticides which are readily isolated when in crystalline form or when associated with spore formation, they have been the subject of a great deal of scientific study, particularly with regard to gene isolation and cloning procedures.

The gene which codes for P-1 has been isolated from B.t. subspecies *kurstaki* strain HD-1-Dipel, and cloned and expressed in *E. coli* [Schnepf et al., U.S. Pat. No. 4,467,036]. The protein product, P-1, was determined to be toxic to a lepidopteran insect (tobacco hornworm larvae). The nucleotide sequence of the promoter region and part of the coding region of the crystal protein gene for P-1 have also been determined [H.P. Wong et al., The Journal of Biological Chemistry, Vol. 258, No. 3, pp.1960–1967 (1983)]. The entire nucleotide sequence of this gene has also been determined and the delta-endotoxin protein itself has been expressed in a transformed *E. coli* strain. [M. J. Adang et al., Gene, Vol, 36, pp.298–300 (1985) and PCT application PCT/US85/01665, for: B.t. Crystal Protein Gene Toxin Segment, (1985)].

The genes for other delta-encotoxin forms have also cloned and expressed in *E. coli*. Recombinant plasmids containing a mosquitocidal delta-endotoxin gene from B.t. var. israelensis were inserted into an E. coli vector. A 26,000-dalton polypeptide was synthesized by E. coli transformed with this vector. This polypeptide was shown to be lethal to insects in the order diptera (mosquitos). [E.S. Ward et al., FEBS Vol. 175, 2, pp.377-382, 1984]. The nucleotide sequence of the gene coding for this crystal protein was also determined along with the resultant protein sequence [C. Waalwijk et al., Nucleic Acids Research, Vol.13, No 22, pp.8207-8217, (1985)]. Another B.t. var. israelensis gene encoding a 130 KDa crystal protein was cloned and used to transform 5 Bacillus megaterium and Bacillus subtilis. Both B. megaterium and B. subtilis expressed crystalline inclusions during sporulation which inclusions were determined to be toxic to the larvae of Aedes aegypti. [V. Sekar et al., Gene, Vol. 33, pp.151-158, (1985)]

Another delta-endotoxin protein crystal was derived from B.t. subspecies sotto. The gene coding for this crystalline protein was cloned in a vector and then expressed in a transformed E. coli. This gene codes for a 144,000 dalton peptide (934 amino acid residues). The nucleotide sequence for the gene and the amino acid sequence of the corresponding protein have been reported. [Y. Shibano et al., Gene, Vol. 34, pp.243-251, (1985)].

It has also been recognized that another major delta-endotoxin protein is produced by several subspecies of B.t. [T. Yamamoto, Biochem. and Biophys. Res. Comm. Vol 103, No. 2, pp.414-421 (1981); T. Yamamoto et al. Archives of Biochemistry and Biophysics, Vol. 227, No. 1, [pp.233-241 (1983)]. This delta-endotoxin has been identified as P-2 and isolated from B.t. var. kurstaki (HD-1). This delta-endotoxin protein has a molecular weight of approximately 65,000 daltons and is known to be toxic to lepidoptera and diptera insects. In contrast, P-1 is active only against insects of the order lepidoptera. To date, although the P-2 protein had been isolated and characterized by its activity against certain insects, the gene coding for this protein and the protein sequence itself, have remained elusive. This fact has rendered it impossible to provide a means for expressing this uniquely active delta-endotoxin protein in an organism other than B.t. The availability of a cloned P-2 gene would enable the enhanced production of the P-2 protein in B.t. and also enable P-2 synthesis in a heterologous organism free of other delta-endotoxins.

SUMMARY OF THE INVENTION

This invention relates to the P-2 delta-endotoxin produced by *Bacillus thuringiensis*, the DNA sequence for the gene which codes for this protein and novel insecticides incorporating this protein and/or organisms transformed with the P-2 gene. More specifically, this invention relates to the cloning and transformation of microorganisms with the gene coding for the P-2 delta-endotoxin. This invention is particularly useful in enabling the expression in organisms other than B.t. of the P-2 delta-endotoxin in quantities greater than that produced by a native P-2 producing B.t. organism during sporulation. In addition, this invention is useful in permitting the transformation of a non-sporulating microorganism with the gene coding for the P-2 toxin so that this delta-endotoxin may be produced during virtually all stages of microorganism growth and, thereby, not be limited to production only during a sporulation stage.

It is an additional object of this invention to provide a homogenous P-2 protein produced by the isolated gene. This protein may be produced by the process of transforming a microorganism, sporulating or non-sporulating, such as *Bacillus megaterium* or E. coli or a different strain of B.t. with the cloned P-2 gene. This process by virtue of selection of the appropriate host and vector would permit high yield production of the P-2 delta-endotoxin such that it is possible to derive a substantially homogenous preparation of the P-2 toxin, i.e. minus any contamination by other varieties of delta-endotoxin typically produced in conjunction with or concurrently with the P-2 toxin in its native B.t. host. The P-2 protein and/or the transformed host may be utilized in a variety of insecticidal compositions.

It is further an object of this invention to provide an organism, other than the native B.t. host, transformed with the DNA coding for the P-2 delta-endotoxin. This foreign transformed host enables the production of the P-2 delta-endotoxin under more desirable and/or selective culturing conditions.

It is another object of this invention to provide a DNA probe useful for detecting the presence of the P-2 gene in the various *Bacillus thuringiensis* strains. This DNA probe also enables the screening of various strains of B.t. for the possible presence of related genes coding for proteins sharing a common homology with the P-2 protein and the isolation of these related genes. All of the above embodiments of this invention will be described in greater detail in the description of the invention which follows.

BRIEF DESCRIPTION OF THE FIGS.

FIG. 2 (parts 1, 2, and 3) shows the DNA nucleotide sequence of the P-2 gene and also the amino acid sequence of the P-2 protein coded for by the DNA nucleotide sequence.

FIG. 3 is comprised of 3A and 3B. 3A is a photograph of an ethidium bromide stained Eckhardt gel. The native plasmids that are present in various strains of B.t are visible illustrating that most strains of B.t. contain several native plasmids. 3B is a photograph of an autoradiogram that was made by hybridizing the radioactively labeled cloned P2 gene with the plasmids shown in 3A. 3B illustrates that the cloned P2 gene hybridized exclusively to a plasmid of 110 MDa in three strains of B.t. that were known to produce P2 protein hybridized to a DNA band of 30 MDa (3B). (HD1-1, HD263-1 and HD278). The cloned P2 gene also hybridized to a DNA band of 30 MDa (3B).

Figure 4A:
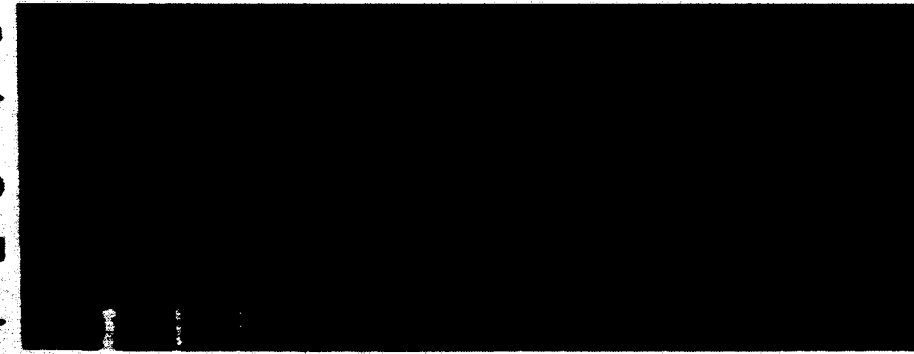
Figure 4B:
Figure 4C:

FIG. 4 is comprised of 4A and 4B. 4A is a photograph of an ethidium bromide stained agarose gel that contains HindIII digested DNA from strains HD1-1, HD263-1, HD267 and HD278. 4A shows that total B.t. DNA that had been digested with HindIII could be resolved into hundreds of different sized fragments. 4B is a photograph of an autoradiogram that was made by hybridizing the radioactively labeled cloned P2 gene with the HindIII fragments shown in 4A. 4C is a photograph of an autoradiogram that was made after re-washing the nitrocellulose filter of 4B at 80.C.

Figure 5:
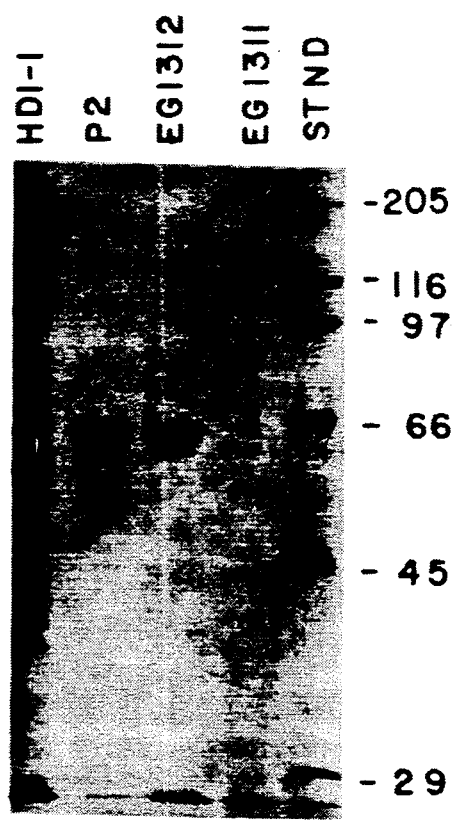

FIG. 5 is a photograph of an SDS/polyacrylamide gel which shows that a recombinant host strain of *Bacillus megaterium* harboring the cloned P-2 gene synthesizes large quantities of a protein having a similar size as that of authentic P-2 protein.

FIG. 6 shows the region of homology between the amino acid sequence of P-1 toxin and P-2 toxin.

DESCRIPTION OF THE INVENTION

Generally stated, the present invention provides for a cloned gene coding for *Bacillus thuringiensis* P-2 delta-endotoxin or toxin and comprising the DNA nucleotide sequence shown in FIG. 2. This gene (which comprises double stranded DNA wherein the nucleotide strands have a complementary base sequence to each other) codes for a protein (or as also used herein equivalently, polypeptide) having the amino acid sequence of the P-2 toxin which amino acid sequence is shown in FIG. 2. The P-2 toxin encoded by the cloned gene has insecticidal activity against lepidoptera and diptera insects.

Methods of producing the P-2 protein are also provided by this invention. In this method of production the P-2 delta-endotoxin gene is inserted into a cloning vector or plasmid which plasmid is then utilized to transform a selected microorganism. The gene may be used with its native promoter, or with a foreign promoter.

The cloning vectors, as described herein, are generally known in the art and are commercially available. The choice of a particular plasmid is within the skill of the art and would be a matter of personal choice. Plasmids suitable for use in this invention are, for instance, pBR322, plasmids derived from B.t., and plasmids derived from *Bacillus* microorganisms and, are those such as, *Bacillus megaterium*. Microorganisms suitable for use with this invention are both sporulating and non-sporulating microorganism such as *E. coli*, B.t., and *Bacillus megaterium*. The microorganisms utilized are also known in the art and are generally available. The choice of any particular microorganism for use in the practice of this invention is also a matter of individual preference. In a preferred embodiment of this invention the microorganism would comprise *Bacillus megaterium*.

Generally stated, the P-2 toxin protein can be produced by a transformed organism and later purified into a homogenous preparation having an amino acid sequence as shown in FIG. 2. More specifically, this protein may be produced by transforming a microorganism with the P-2 gene, growing the transformed microorganism so that the protein coded for by the P-2 gene is expressed in the microorganism and by extracting the protein from the organism with standard protein purification techniques. It is also within the scope of this invention that the protein not be separated from the transformed microorganism but that this organism, including the expressed P-2 protein, be utilized as or in an insecticidal composition.

This invention also provides for a novel insecticide for use against lepidoptera and diptera comprising a mixture of B.t. P-2 toxin and a suitable carrier. The P-2 toxin may be contained in the organism or as part of spores, or be a homogenous protein preparation or in a mixture of spores with cultured transformed organisms. The P-2 toxin may also be contained in a non-sporulating microorganism or a sporulating microorganism such as *Bacillus megaterium* or B.t. A suitable carrier may be any one of a number of solids or liquids known to those of skill in the art.

This invention also comprises the recombinant vectors or plasmids including the P-2 gene and the particular microorganisms which have been transformed with this gene. In addition, this invention also provides for oligonucleotide probes for the gene coding for the P-2 delta-endotoxin. All of these aspects of the inventions are described in detail below and illustrated in the following examples.

Recombinant DNA Technology and Gene Expression

Generally stated, recombinant DNA technology involves insertion of specific DNA sequences into a DNA vehicle (plasmid or vector) to form a chimeric DNA molecule which is capable of replication in a host cell. The inserted DNA sequence is typically foreign to the recipient host, i.e, the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules, For example, U.S. Pat. No. 4,237,224 to Cohen and Boyer describes production of such recombinant plasmids using restriction enzymes and methods known as ligation. These recombinant plasmids are then introduced and replicated in unicellular organisms by means of transformation. Because of the general applicability of techniques described therein, U.S. Pat. No. 4,237,224 is hereby incorporated by reference into the present specification.

Regardless of the method used for construction, the recombinant DNA molecule must be compatible with the host cell, i.e., capable of autonomous replication in the host cell. The recombinant DNA molecule should also have a marker function which allows the selection of host cells so transformed by the recombinant DNA molecule. In addition, if all of the proper replication, transcription and translation signals are correctly arranged on the chimeric DNA molecule, the foreign gene will be expressed in the transformed cells and their progeny.

These different genetic signals and processing events control many levels of gene expression, i.e., DNA transcription and messenger RNA translation. Transcription of DNA is dependent upon the presence of a promoter which is a DNA sequence that directs the binding of RNA polymerase and thereby promotes transcription.

Translation of messenger RNA (mRNA) in procaryotes depends upon the presence of the proper procaryotic signals. Efficient translation of mRNA in procaryotes, such as B.t., requires a ribosome binding site called the Shine Dalgarno (SD) sequence on the mRNA. This sequence is a short nucleotide sequence of mRNA that is located before the start codon (AUG) which encodes the amino-terminal methionine of the protein. The SD sequences are complementary to the 3'-end of the 16S RNA (ribosomal RNA) and probably promote binding of mRNA to ribosomes by duplexing with the mRNA to allow correct positioning of the ribosome (Roberts and Lauer, 1979, Methods in Enzymology, 68:473).

One method widely employed for the cloning of a particular gene is to prepare a "library" of recombinant plasmids. Each recombinant plasmid is comprised of a plasmid vector, which usually confers antibiotic resistance to cells that harbor it, plus a fragment of DNA from the donor organism, an organism that contains the gene. The plasmid library is commonly prepared by digestion of both the plasmid vector and total DNA from the donor organism with a restriction enzyme, inactivation of the enzyme and ligation of the DNA mixture The ligated DNA is a plasmid library. The key feature of this plasmid library is that it contains many different recombinant plasmids. It is highly likely that at least one of the recombinant plasmids in the library will contain a fragment of DNA from the donor organism on which the gene of interest resides. The plasmid library is transformed into the cells of a host organism that does not contain the gene. The host cells are spread on a selective solid medium, usually one containing an antibiotic, that allows only transformed cells, those containing recombinant plasmids, to grow into colonies. Individual transformed host colonies are tested for the acquisition of the gene from the donor organism. In host colonies the acquired gene is carried on the recombinant plasmid.

One of the most direct methods of testing for the acquisition of a gene is to use a gene-specific hybridization probe, a fragment of DNA that is homologous to the gene. A characteristic of homologous DNA fragments is that they will bind tightly to each other during hybridization. Typically a radioactively labeled DNA probe is used during hybridization so that binding of the probe to the gene can be easily monitored.

A recent advance in molecular biology is the use of synthetic oligonucleotides as gene-specific probes. The basis for the use of the oligonucleotides is that in all biological systems a particular sequence of nucleotides encodes a precise sequence of amino acids. Conversely if the sequence of amino acids is known for a particular protein then the nucleotide sequence encoding the protein can be inferred, although not precisely. In practice, the partial amino acid sequence of a protein, the product of the gene of interest, is determined by chemical methods. Based on the protein amino acid sequence a gene-specific oligonucleotide probe is synthesized that may be, to varying degrees, homologous to the gene. Exact homology cannot be guaranteed because knowledge of the amino acid sequence of a protein does give exact knowledge of the nucleotide sequence of the gene encoding the protein. Nevertheless, even though the homology between the oligonucleotide probe and the gene may not be precise, hybridization conditions can usually be found that will permit the oligonucleotide probe to bind specifically to the gene.

Accordingly, in isolating the P-2 gene, the P-2 protein was purified from a donor strain of *B. thuringiensis* var. kurstaki, and the partial amino acid sequence of the P-2 protein was determined. A P-2 gene-specific oligonucleotide probe was synthesized based on the amino acid sequence of the P-2 protein. The oligonucleotide was radioactively labeled and was used in hybridization experiments to identify transformed host colonies that harbored recombinant plasmids carrying the P-2 gene from the donor B.t. strain.

Cloning of the P-2 Toxin Gene From *Bacillus Thuringiensis* Strain HD263-1

More specifically, in order to clone the P-2 toxin gene of this invention, cells of B.t. strain HD1-1, a single colony isolate immediately derived from parent strain HD-1 (U.S.D.A., Cotton Insect Research Unit, Brownsville, Texas 78520), were grown in C2 media (1% Glucose, 0.2% Peptone, 0.5% N Z Amine A, 0.2% Yeast 1 Extract, 15mM $(NH_4)_2SO_4$, 23mM $KH_2PO_4$, 27mM $K_2HPO_4$, 1 mM $MgSO_4.7H_2O$, 600uM $CaCl_2$, 17uM $ZnSO\ 7H_2O$, 17uM $CuSO_4.5H_2O$, 2uM $FeSO_4.7H_2O$) at 30° C. until t72 (hours) and spores plus crystals were harvested by centrifugation. The spore/crystal pellet was washed with several changes of 1 M NaCl and then several changes of deionized water. Toxin proteins were solubilized by incubating the spore/crystal preparation in 5% B-mercaptoethanol, 2% NaDodeS04, 60 mM Tris pH 6.8, 10% glycerol at 70 degrees C. for 7 min., and spores were removed by centrifugation. The supernatant was electrophoresed through polyacrylamide gels containing NaDodeSO4 to separate proteins. The gel was stained with Coomassie dye and gel slices containing the P-2 protein were cut out with a razor blade. The homogeneous P-2 protein preparation was electroeluted from gel slices and, after acetone precipitation, the $NH_2$-terminal amino acid sequence of the P-2 protein was determined by automated Edman degradation carried out on an Applied Biosystems Gas Phase Sequenator (model 470A) and analyzed on a DuPont Zorbax C18 column in a Hewlett-Packard HPLC (model 1090) with a 1040 diode array detector. The amino acid sequence of the $NH_2$ terminal portion of the homogeneous P-2 protein was determined to be:

| 1 | 2 | 3 | 4 | 5 | 6 | 7 | 8 | 9 | 10 |
|---|---|---|---|---|---|---|---|---|---|
| MET | ASN | ASN | VAL | LEU | ASN | SER | GLY | ARG | THR |
| 11 | 12 | 13 | 14 | 15 | 16 | 17 | 18 | 19 | 20 |
| THR | ILE | ASN | ASP | ALA | TYR | ASN | VAL | VAL | ALA |
| 21 | 22 | 23 | 24 | 25 | 26 | | | | |
| HIS | ASP | PRO | PHE | SER | GLY | | | | |

Oligonucleotide Problem for the P-2 Gene

A 62 mer oligonucleotide probe encoding amino acids 4 through 24 of the NH2-terminus of the P-2 protein was synthesized on an Applied Biosystems DNA synthesizer (model 380A). It was recognized that because of the codon degeneracy (certain amino acids are each encoded by several slightly different codons) the sequence of the synthetic oligonucleotide would probably be different from the actual NH2-terminal sequence of the P-2 gene. However, the fact that the B.t. genome is 68% A:T and the codon usage information for previously cloned and sequenced B.t. genes were used in designing an oligonucleotide probe that would have the highest probability of matching the actual sequence of the P-2 gene. The oligonucleotide probe was designed to bind only to the NH2-terminal coding region of the P-2 gene. The sequence of the P-2 gene-specific oligonucleotide probe was:

5'-GTA TTA AAT TCA GGA AGA ACA ACA
ATT AAT GAT GCA TAT AAT GTA GTA
GCA CAT GAT CCA TT-3'.

In addition to enabling the original isolation of the P-2 gene herein, this DNA probe also comprises another preferred embodiment of this invention. This DNA probe permits the screening of any B.t. strain to determine whether the P-2 gene (or possibly a related gene) is naturally present or whether a particular transformed organism includes the P-2 gene. In this fashion it is also possible to estimate the insectididal activity of that strain of B.t. It is also within the scope of this invention that this probe may comprise a smaller or larger oligonucleotide. The probe may be labeled by any number of techniques known in the art(such as radioactively or enzymatically labeled) and as described below.

Construction of a Plasmid Library enriched for the P-2 Gene

The oligonucleotide probe was used to determine the size of a restriction fragment of B.t. DNA that contained at least the NH2-terminal coding region of the P-2 gene. For this determination strains HD263-1, a single colony isolate immediately derived from parent strain HD-263 (U.S.D.A., Cotton Insect Research Unit, Brownsville, Texas 78520), and strain HDl-1, a single colony isolate immediately derived from patent strain HD-1 (U.S.D.A., Brownsville, Texas) were used as a source of DNA. Both of these strains were known to produce the P-2 crystal protein. B.t. strains EG2158 and HD567 which do not produce P-2 crystal protein were used as negative controls.

DNA was isolated from the various donor strains after growth of the cells to mid-log phase at 30 C in LB medium. Cells were harvested by centrifugation, resuspended in 50mM Tris HCl pH 7.8, 10mM EDTA, 1 mg/ml lysozyme and incubated at 37° C. for 60 min. Cells were lysed by adding $NaDodeSO_4$ to a final concentration of 0.2%. Cell lysates were extracted twice with an equal volume of phenol and once with an equal volume of chloroform/isoamyl alcohol (24/1). One tenth volume of 3 M NaAcetate and 2 volumes of EtOH were added to the lysates and DNA was extracted by spooling on a glass rod. The spooled DNA was soaked in 66% EtOH for 5 min. and in diethyl-ether for 1 min. The spooled DNA was air dried and resuspended in deionized water.

Hybridization experiments were performed by digesting total DNA from each of the donor strains with HindIII restriction enzyme, electrophoresing the digested DNA on an agarose gel and transferring the DNA from the agarose gel to a nitrocellulose filter by the blot technique of Southern (J. Molec. Biol. 98:503–517, 1978). The nitrocellulose filter was incubated at 32° C. for 16 hrs. in a solution of 3 X SSC (1 $\times$SSC =0.15M NaCl/0.015 M Sodium Citrate), 0.1 % $NaDodeSO_4$, 200 ug/ml heparin, 10 X Denhardt's (1$\times$=0.02% Bovine Serum Albumin/0.02% Ficoll/0.02% Polyvinyl-Pyrrolidone) containing approximately 1 ug of the P2 gene-specific oligonucleotide probe that had been radioactively labeled with gamma-P32-ATP and T4 kinase. After hybridization the nitrocellulose filter was washed with 3$\times$SSC, 0.1 % $NaDodeSo_4$ at 32° C. for one hour and the filter was exposed to X-ray film. The resulting autoradiogram showed that the oligonucleotide probe specifically hybridized to two HindIII fragments of DNA, from strain HD263-1, of approximately 9.0 and 5.0 kb. The probe hybridized to apparently identical 9.0 and 5.0kb HindIII fragments of DNA from strain HDl-1. The probe failed to hybridize to any DNA restriction fragments from two strains of B.t. that did not synthesize P-2 crystal protein, EG258 and HD567.

It was necessary to determine which of the two HindIII fragments, 9.0 or 5.0 kb, hybridized most strongly to the oligonucleotide probe since the most strongly hybridizing fragment would be most likely to contain the P-2 gene. Strength of hybridization is measured by the highest wash temperature at which the probe remains bound to the DNA fragment on the nitrocellulose filter. Accordingly the nitrocellulose filter was repeatedly washed in 3$\times$SSC, 0.1 % $NaDodeSO_4$ at progressively higher temperatures, each wash being followed by autoradiography, until a temperature was reached (50° C.) at which the radioactive probe no longer hybridized to the 9.0 kb fragment but was seen to hybridize exclusively to the 5.0 kb band. Therefore, it was determined that at least the NH2-terminal coding region of the P-2 gene resided on the 5.0 kb HindIII fragment of DNA from strains HD263-1 and HDl-1.

A P-2 gene-enriched plasmid library was constructed by digesting HD263-1 total DNA with HindIII, electrophoresing the digested DNA on an agarose gel and excising gel slices containing HindIII DNA fragments ranging in size from approximately 4 0 to 6.0 kb. HD263-1 HindIII fragments ranging in size from 4.0 to 6.0 kb were electroeluted from agarose gel slices, phenol plus chloroform extracted, ethanol precipitated and ligated into the HindIII site of plasmid pBR322 that had been digested with HindIII and treated with alkaline phosphatase. Alkaline phosphatase greatly increased the probability that recombinant plasmids were formed consisting of pBR322 plus a HindIII fragment of HD263-1 DNA. The resulting ligation mix consisted of a library of recombinant plasmids enriched for the P-2 toxin gene from strain HD263-1.

Colony Hybridization and Isolation of a 5.2 kb HindIII Fragment containing the P-2 Gene The P-2 gene-enriched plasmid library was transformed into an ampicillin sensitive host strain of *E. coli*, HB101 (Bethesda Research Laboratories, Bethesda, MD.), by the $CaCl_2$ procedure. *E. coli* strain HB101 does not synthesize P-2 protein and, therefore, it would not be expected to contain the P-2 gene. *E. coli* was used as the host strain because these cells are easily transformed with recombinant plasmids. All host cells acquiring a recombinant plasmid would become ampicillin resistant. After exposure to the recombinant plasmids the *E. coli* host cells were spread onto solid medium containing ampicillin and those cells that harbored a recombinant plasmid were able to grow into colonies. It was expected that each individual ampicillin resistant host colony would harbor many identical copies of a recombinant plasmid comprised of pBR322 plus a unique HindIII fragment from the donor strain HD263-1 DNA. However, the donor strain HindIII fragment in the recombinant plasmid would differ from one colony to the next.

Approximately two thousand individual ampicillin resistant colonies were blotted onto nitrocellulose filters. Replicas of the colonies were saved for later use as described below. The recombinant plasmids contained in the colonies were bound to the nitrocellulose filters by treating the colonies with NaOH and $NH_4$Acetate. The resulting nitrocellulose filters contained an array of recombinant plasmids each of which was physically separated from other recombinant plasmids. The nitrocellulose filters were hybridized at 50.C for 16 hours in a solution of 3$\times$SSC, 200 ug/ml heparin, 0.1% $NaDodeSO_4$, 10 $\times$Denhardt's and approximately 1 ug of the P2 gene-specific oligonucleotide probe that had been radioactively labeled. The filters were washed at 50.C for one hour in 3$\times$SSC, 0.1% $NaDodeSO_4$ and were exposed to x-ray film. The resulting autoradiogram showed that the oligonucleotide probe had hybridized to recombinant plasmids at four different locations on the nitrocellulose filters.

By aligning the autoradiogram with the colony replicas it was possible to identify four colonies whose recombinant plasmids had apparently hybridized with the oligonucleotide probe.

The recombinant plasmids were extracted from each of the four colonies. The plasmids were digested with HindIII and electrophoresed on an agarose gel. Three of the four plasmids consisted of pBR322 plus an apparently identical sized 5.2 kb HindIII fragment of HD263-1 DNA. The plasmids were transferred from the agarose gel to a nitrocellulose filter by the blot procedure of Southern. The nitrocellulose filter was hybridized with the radioactively labeled oligonucleotide probe and exposed to x-ray film. The resulting autoradiogram showed that the oligonucleotide probe hybridized exclusively to the 5.2 kb HindIII fragment in each of the three recombinant plasmids. One of these recombinant plasmids, designated pEG201, was selected for further experimentation and evaluation. The original *E. coli* colony harboring pEG 201 was designated EG 1304.

Location of the P-2 Gene on the Cloned 5.2 KB HindIII Fragment

It was likely that the cloned 5.2 kb HindIII fragment contained at least the NH2-terminal coding region of the P-2 gene. Presence of the P-2 gene on the 5.2 kb fragment was verified using DNA sequencing to search for a region in the cloned 5.2 kb fragment that encoded the NH2-terminus of the P-2 protein. Since it is difficult to sequence a fragment of DNA longer than two kb it was necessary to identify a smaller fragment of DNA within the 5.2 kb fragment that would be expected to contain the P-2 gene. Accordingly plasmid pEG201 was digested with various restriction enzymes, digested plasmid was electrophoresed through an agarose gel and plasmid restriction fragments were blotted from the gel to a nitrocellulose filter. Hybridization of the filter with the radioactively labeleled oligonucleotide probe revealed that the probe specifically hybridized to a 1.3 kb Sau3A Restriction fragment of DNA. Therefore, it was expected that the 1.3 kb fragment would contain at least the NH2-terminal coding region of the P-2 gene.

The 1.3 kb fragment was subcloned from pEG201 into the DNA sequencing vectors mp18 and mp19 (Bethesda Research Laboratories, Bethesda MD). DNA sequencing of the 1.3 kb fragment revealed that it contained a region of DNA that encoded the NH2-terminus of the P-2 protein. This conclusively demonstrated that the cloned 5.2 kb HindIII fragment from the donor strain HD263-1 contained the P-2 gene. Additional DNA sequencing of the 1.3 kb fragment showed that an AccI restriction site was located 150 nucleotides upstream from the NH2-terminal methionine codon of the P-2 gene. The position of this AccI site served as a marker. It allowed the location of the P-2 gene in the 5.2 kb fragment to be precisely determined as described below.

Figure 1:
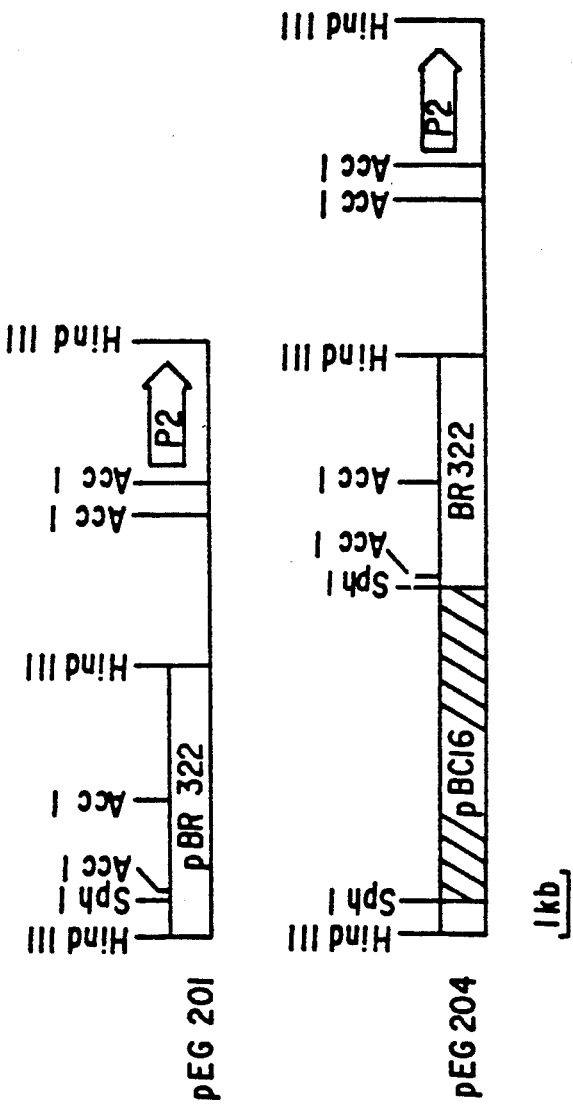
FIG. 1 is a restriction map of the recombinant plasmids pEG 201 and pEG 204 that contain the cloned P-2 gene. The location and direction of transcription of the P-2 gene are indicated by the large arrow.

The location and direction of transcription of the P-2 gene on the cloned 5.2 kb fragment was determined by digesting the 5.2 kb fragment with AccI in combination with various other restriction enzymes. The restriction fragments were electrophoresed through an agarose gel and blotted onto a nitrocellulose filter. By hybridizing the filter with the radioactively labeled P2 gene-specific oligonucleotide probe it was possible to determine the location and orientation of various restriction fragments on the larger 5.2 kb fragment. From this knowledge the precise position and direction of transcription of the P-2 gene on the 5.2 kb fragment was determined as indicated by the arrow in FIG. 1. FIG. 1 shows a restriction map of plasmid pEG201. The boxed areas denote plasmid vector DNA. pBR322 vector is indicated by an open boxed area. The horizontal line denotes cloned B.t. DNA from strain HD263-1. The large arrow indicates the coding region of the P2 gene. Plasmid pEG204 is described below. The length of the P-2 gene was estimated to be approximately 1.9 kb based on the estimated size (68 kDa) of the P-2 protein.

DNA Sequence of the Cloned P-2 Gene

It was estimated that all or at least most of the P-2 gene was contained in the 2.2 kb AccI - HindIII fragment within the cloned 5.2 kb fragment (FIG. 1). Accordingly, the 2.2 kb AccI - Hind III fragment was subcloned into the sequencing vectors mp18 and mp19 and the complete sequence of the 2.2 kb fragment was determined by the dideoxy procedure of Sanger (Sanger, F., Nicklen, S. & Coulson, A.R. (1977) Proc. Natl. Acad. Sci. USA 74:5463–5467). As expected the 2.2 kb fragment contained an open reading frame (protein coding region) that began with the NH2-terminal codons for the P-2 protein. The DNA sequence of the 2.2 kb fragment, which includes the P-2 gene of this invention, and the deduced amino acid sequence of the P-2 protein are shown in FIG. 2. FIG. 2 shows the complete DNA sequence of the 2.2. kb AccI - HindIII fragment beginning with the first nucleotide of the AccI site and ending with the last nucleotide of the HindIII site. The AccI site is located 150 nucleotides upstream from the NH2-terminal methionine codon of the P-2 gene.

Use of the Cloned P-2 Gene as a Specific Hybridization Probe

Identification of Native B.t. Plasmids containing P-2 Genes

One advantage of a cloned DNA sequence is that it can be used to identify related DNA sequences in uncharacterized samples of DNA. In the case of the P-2 gene it is now possible that the cloned gene can be used to detect the presence of a P-2 gene in a strain of B.t. Most strains of B.t. contain numerous native plasmids in addition to chromosomal DNA. For many of these strains it is not known if the P-2 gene resides on the chromosome or on one of the plasmids.

In order to determine whether the cloned P-2 gene could be used to detect the locations of a P-2 gene in a native B.t. host strain, B.t. strains HD263-1, HD1-1, HD567 and HD278 were lysed according to the procedure of Eckhardt (Eckhardt, T. (1978) Plasmid 1:584–588) and t he lysates were electrophoresed through agarose gels. This procedure allowed the separation by size of all plasmids contained in a particular strain. The separated plasmids were transferred from the agarose gel to a nitrocellulose filter by the blot procedure of Southern. The nitrocellulose filter was hybridized with the radioactively labeled 2.2kb AccI - HindIII (P-2 gene) fragment. Autoradiography of the nitrocellulose filter revealed that the P-2 gene fragment hybridized exclusively to one plasmid of approximately 110 MDa in the P2-producing strains HD263-1, HD1-1 and HD278 (FIG. 3). The cloned P-2 gene did not hybridize to any plasmids in the P-2-negative strain HD567. Therefore, this experiment demonstrated that the cloned P-2 gene can be used in a direct manner to identify native plasmids containing P-2 genes in B.t. strains. DNA hybridization with the cloned P-2 gene allowed direct identification of a single plasmid carrying a P-2 gene out of many such plasmids existing in strains of B.t.

Identification of DNA Restriction Fragments containing P-2 Genes

The cloned P-2 gene from B.t. strain HD263-1 was contained on a 5.2 kb HindIII fragment of DNA. A procedure was conducted in order to determine whether the cloned P-2 gene could be used to identify similar DNA restriction fragments containing P-2 genes from other strains of B.t. Accordingly, total DNA from the test strains HDl-1, HD278, HD567 and the original donor strain HD263-1 were digested with HindIII restriction enzyme, the digested DNA was electrophoresed through an agarose gel and digested DNA was transferred from the gel to a nitrocellulose filter. The filter was hybridized at 55.C with the radioactively labeled 2.2 kb AccI - HindIII DNA (P-2 gene) fragment and, after washing at 55.C, the filter was exposed to x-ray film.

FIG. 3 (3A) is a photograph of an ethidium bromide stained Eckhardt gel. The native plasmids that are present in various strains of B.t. are visible. 3A illustrates that most strains of B.t. contain several native plasmids. The numbers to the left of the figure indicate the size in megadaltons (MDa) of the plasmids.

FIG. 3 (3B) is a photograph of an autoradiogram that was made by hybridizing the radioactively labeled cloned P-2 gene with the plasmids shown in 3A. 3B illustrates that the cloned P-2 gene hybridized exclusively to a plasmid of 110 MDa in three strains of B.t. that were known to produce P-2 protein (HD-1, HD263-1 and HD278). The cloned P2 gene also hybridized to a DNA band of 30 MDa (FIG. 3 (3B)). This DNA band was DNA fragments that resulted from the breakdown of the 110 MDa plasmid. Very large plasmids such as the 110 MDa plasmid are often broken down into smaller fragments during electrophoresis through Eckhardt-type gels. Specific hybridization of the cloned P-2 gene to the 110 MDa plasmids indicates that for strains HDl-1, HD263-1 and HD278 only the 110 MDa plasmids carry the P-2 gene. The cloned P2 gene did not hybridize to any plasmids from a strain that did not produce P2 protein (HD567). Overall, FIG. 3 (3A and 3B) demonstrate that the cloned P-2 gene can be used as a specific probe for the identification of P-2 genes on native B.t. plasmids.

FIG. 4 (4A) is a photograph of an ethidium bromide stained agarose gel that contains HindIII digested DNA from strains HDl-1 (lane 2), HD567 (lane 3), HD278 (lane 4) and HD263-1 (lane 5). FIG. 4 (4A) shows that total B.t. DNA that had been digested with HindIII could be resolved into hundreds of different size fragments. The lane marked 1 contained Lambda DNA that had been digested with HindIII. This serves as a size marker. The numbers to the left indicate the size in kilobase (kb) of the DNA fragments.

FIG. 4 (4B) is a photograph of an autoradiogram that was made by hybridizing (at 55.C) the radioactively labeled cloned P-2 gene with the HindIII fragments shown in 4A. Overall, FIG. 4 (4A and 4B) demonstrate that cloned P-2 gene can be used as a specific probe for the identification of DNA restriction fragments that contain P-2 genes.

Autoradiography showed that, as expected, the cloned P-2 gene hybridized to a 5.2 kb HindIII fragment from strain HD263-1 (FIG. 4, (4B) Lane 5). Surprisingly, the P-2 gene also hybridized to a 9.0 kb HindIII fragment from strain HD263-1 (FIG. 4(4B), lane 5). The P-2 gene hybridized to 5.2 and 9.0 kb HindIII fragments in strain HDl-1 (FIG. 4(4B), lane 2), and to HindIII fragments of 5.2 and 4.4 kb in strain HD278 (FIG. 4(4B) lane 4). The P-2 gene failed to hybridize to any HindIII fragments from the P-2-negative strain HD567 (FIG. 4(4B), lane 3). The nitrocellulose filter was rewashed at 80.C and exposed to x-ray film. The resulting autoradiogram showed that, after the higher wash temperature, significantly less of the labeled P-2 gene probe was bound to the 9.0 and 4.4 kb fragments than to the 5.2 kb fragment (FIG. 4(4C), Lanes 2, 4 and 5).

The above demonstrates several preferred uses of the cloned P-2 gene. First the cloned P-2 gene from strain HD263-1 can be used to identify DNA restriction fragments containing P-2 genes from other B.t. strains. For example the cloned P-2 gene hybridized to two HindIII fragments from strain HDl-1. Second the cloned gene permits determination of the number of P-2 genes present in a particular B.t. strain. For example strain HD263-1 was found to contain two P-2 genes since the P-2 gene probe hybridized to two HindIII restriction fragments from strain HD263-1. It is significant that the P-2 gene specific oligonucleotide probe also hybridized to two HindIII fragments of 9.0 and 5.2 kb from strain HD263-1.

The precise nature of the P-2 gene on the 9.0 kb fragment cannot be known until the 9.0 kb fragment is isolated and its DNA sequence determined. This leads to a third preferred use for the cloned P-2 gene. Since the P-2 gene specifically hybridized to a 9.0 kb HindIII fragment the cloned P-2 gene (or portions or derivatives thereof) is therefore, an ideal probe for the isolation of this fragment.

Fourth, the cloned P-2 gene permits rapid qualitative estimation of the relatedness between P-2 genes. For example, it would be estimated that the cloned P-2 gene is more related to the P-2 gene contained on the 5.2 kb fragment of strain HDl-1 than to the P-2 genes contained on either the 9.0 or 4.4 kb HindIII fragments. This relatedness was directly demonstrated by the stronger hybridization at 80.C of the P-2 gene probe to the 5.2 kb fragment than to either the 9.0 or 4.4 kb fragments.

Additional Purification of P-2 Toxin

The P-2 gene can be inserted in any appropriate plasmid which may then be utilized to transform an appropriate microorganism. It is clearly within the scope of this invention that microorganisms other than B.t. may be transformed by incorporation of the P-2 gene i.e., generally stated, organisms from the genera *Bacillus, Escherichia*, and *Cyanobacteria*. Preferred for use with this invention are organisms *Bacillus megaterium* and *Escherichia coli*. It is also within the scope of this invention that different strains of B.t. may also be transformed by the incorporation of the P-2 gene.

The microorganisms so transformed will preferably produce P-2 in quantities that are far in excess of the quantity of P-2 produced in a B.t. natural host strain. The P-2 produced by a transformed organism is preferably the only delta-endotoxin produced by that organism. In this manner, the organism itself may be utilized alone or as part of an insecticidal composition. Since P-2 would preferably be the only delta-endotoxin produced by the organism, it is a straightforward process to purify the P-2 from other cellular material by methods known in the art such as renografin density gradients.

Transformation of P-2 into Plants

It is also within the scope of this invention that the P-2 gene (FIG. 2) be inserted directly into a plant so that the plant itself produces the P-2 toxin.

Genetic engineering of plants may be accomplished by introducing the desired DNA containing the P-2 gene into plant tissues or cells using DNA molecules of a variety of forms and origins. These include, but are not limited to: DNA molecules derived from naturally occurring plant vectors such as the Ti plasmid from *Agrobacterium tumefaciens* or plant pathogens such as DNA viruses like Cauliflower Mosaic virus (CaMV) or Geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components (e.o., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants).

DNA containing the P-2 gene may be delivered into the plant cells or tissues directly by infectious plasmids, such as Ti, viruses or microorganisms like *A. tumefaciens*, the use of liposomes, microinjection by mechanical methods and by whole chromosomes or chromosome fragments.

Products and Formulations Incorporating the P-2 Protein

The P-2 delta-endotoxin is a potent insecticidal compound with activity against lepidopteran and dipteran insects. It is, therefore, within the scope of the invention that the P-2 protein toxin be utilized as an insecticide (the active ingredient) alone, preferably in homogenous or pure form and having the amino acid sequence of FIG. 2, or as included within or in association with a transformed microorganism which expresses a cloned P-2 gene or in a mixture of B.t. or other transformed sporulating microorganisms containing P-2 in spores or otherwise. The compositions of the invention containing P-2 are applied at an insecticidally effective amount which will vary depending on such factors as, for example, the specific lepidopteran or dipteran insects to be controlled, the specific plant to be treated and the method of applying the insecticidally active compositions. The preferred insecticide formulations are made by mixing P-2 alone or incorporated in or associated with a transformed organism, with the desired carrier. The formulations may be administered as a dust or as a suspension in oil (vegetable or mineral) or water, a wettable powder or in any other material suitable for agricultural application, using the appropriate carrier adjuvants. Suitable carriers can be solid or liquid and correspond to the substances ordinarily employed in formulation technology, e.g., natural or regenerated mineral substances, solvents, dispersants, wetting agents, tackifiers, binders or fertilizers.

The formulations containing a solid or liquid adjuvant, are prepared in known manner, e.g., by homogenously mixing and/or grinding the active ingredients with extenders, e.g., solvents, solid carriers, and in some cases surface active compounds (surfactants).

Suitable liquid carriers are vegetable oils, such as coconut oil or soybean oil, mineral oils or water. The solid carriers used, e.g., for dusts and dispersible powders, are normally natural mineral fibers such as calcite, talcum, kaolin, or attapulgite. In order to improve the physical properties it is also possible to add highly dispersed silicic acid or highly dispersed absorbent polymers. Suitable granulated adsorptic carriers are porous types, for example pumice, broken brick, sepliolite or bentonite. Suitable nonsorbent carriers are materials such as silicate or sand. In addition, a great number of pregranulated materials or inorganic or organic mixtures can be used, e.g., especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures or surfactants.

Suitable anionic surfactants can be both water-soluble soaps and water-soluble synthetic surface active compounds.

Suitable soaps are the alkali metal salts, alkaline earth metal salts or unsubstituted ammonium salts of higher fatty acids ($C_{10}$-$C_{11}$), e.g., the sodium or potassium salts of oleic or stearic acid, or natural fatty acid mixtures which can be obtained, e.g., from coconut oil or tallow oil. Further stable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the forms of alkali metal salts, alkaline earth metal salts or unsubstituted ammonium salts and generally contain a $C_6$-$C_{22}$ alkyl, e.g., the sodium or calcium salt of dodecylsulfate, or of a mixture of fatty alcohol sulfates, obtained from fatty acids. These compounds also comprise the salts of sulfonic acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g., salts of the phosphoric acid ester of an adduct of p-nonylphenol with 4 to 14 moles of ethylene oxide.

Nonionic surfactants are preferably a polyglycol ether derivative or aliphatic or cycloaliphatic alcohol or saturated or unsaturated fatty acids and alkylphenols, said derivative containing 3 to 10 glycol ether groups and 8 to 20 carbon atoms in the (aliphatic) hydrocarbon moiety and 6 to 18 carbon atoms in the alkyl moiety of the alkylphenols.

Other suitable non-ionic surfactants are the water soluble adducts of polyethylene oxide with alkylpropyleen glycol, ethylenediaminopolypropylene glycol and alkylpolypropylene glycol contain 1 to 10 carbon atoms in the alkyl chain, which adducts contain 20 to 250 ethylene glycol ether groups and 10 to 100 propylene glycol ether groups.

Representative examples of non-ionic surfactants are nonylphenolpolyethyoxyethanols, castor oil, glycol ethers, polypropylene/polyethylene oxide adducts, tributylphenoxypolyethoxyethanol, ethylene glycol and octylphenoxypolyethoxynethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as substituents on the nitrogen, as least one $C_8$–$C_{22}$ alkyl radical and, as further substituents, lower unsubstituted or halogenated alkyl benzyl, or hydroxylated lower alkyl radicals. The salts are preferably in the form of halides, methyl sulfates or ethylsulfates, e.g., stearyltrimethylammonium chloride.

Concensus Delta-Endotoxin Protein Homology

A computer search was conducted to determine whether the P-2 gene was homologous to any other genes whose sequences had been published. No DNA sequence homology was found between the P2 gene and other genes. However, surprisingly a degree of amino acid sequence homology was found to exist between the P2 and P1 proteins. FIG. 6 shows that the P2 ad P1 proteins shared a region of 37% homology over a stretch of about 100 amino acids.

Sequences of conserved amino acids that are found within otherwise non-homologous proteins often signal important functional domains for the proteins. It is foreseeable that the conserved amino acids shown in FIG. 6 constitute an "active site" that is responsible for the lepidopteran larvicidal activities of the P1 and P2 proteins. Therefore, this protein has utility in site specific mutagenesis experiments to effect or change the amino acid composition so as to more specifically target a resultant change in toxicity.

The importance of this stretch of 100 amino acids can be determined by subcloning the 300-bp fragment of DNA that encodes these amino acids. This procedure would also yield a means for producing this protein in B.T., B.megaterium or E. coli. Subcloning may be accomplished by using site-specific in vitro mutagenesis to create restriction sites bordering the 300-bp fragment of DNA coding for this one-hundred amino acid protein. These restriction sites could then be used to precisely excise the DNA fragment. The DNA fragment could then be inserted downstream from a promoter and ribosome binding site on a Bacillus or other appropriate vector. The Bacillus vector could be genetically engineered in such a way that it would contain the promoter and ribosome binding site of the P2 gene itself. The resulting recombinant plasmid could then be transformed into an appropriate Bacillus strain (or other appropriate organism as described herein) and the larvicidal activity of the recombinant strain could be measured. The transformed organism would also serve as a means for producing this protein. The transformed organism or the protein itself or both in admixture may be utilized in an insecticidal composition in the same manner as the P2 toxin protein.

It is possible that the 100 amino acid polypeptide that would be synthesized from the recombinant plasmid would be degraded by proteases within the Bacillus cell. To circumvent this potential problem a protease negative strain of Bacillus could be used for expression such as the one described by Wong et al. (Wong, S., Kawamura, F., and Doi, R. 1986 J. Bacteriol. 168:1005–1009).

EXAMPLES

The insecticidal activity of transformed or non-transformed Bacillus megaterium and of Escherichia coli was determined by including various amounts of these microorganisms in a test diet which was fed to insects. After feeding, insect mortality was measured. Specifically, this involved growing the microorganism to stationary phase on solid agar Base media for two days at 30° C. For E. coli harboring plasmids the media was LB containing 40 ug/ml ampicillin. For B. meqaterium harboring plasmids the media was DS containing 10 ug/ml tetracycline. The microorganisms were harvested from the solid medium by scraping with a spatula. The wet weight of the harvested bacteria was determined and bacterial cells were resuspended to a known concentration in deionized water. Serial dilutions of the suspended bacterial cells were made and 200 ul of each dilution was topically applied to 3 ml of a solid agar-based artificial diet in a feeding cup. The top surface area of the diet was 600 square millimeters. In the case of Heliothis the diet contained soy flour and for Lymantria dispar the diet contained wheat germ. One neonate larva was placed in each feed cup and mortality was scored after seven days.

The LC50 value (weight of bacterial cells required to kill 50% of the larvae) was calculated from a probit analysis of insect mortality (R.J. Daum., A Revision of Two Computer Programs for Probit Analysis. Bulletin of the Entomological Soc. of America, vol 16(1), pp. 10–15).

Example 1—Bioassay of the Expression Product of the Cloned P2 Gene in E. Coli Heliothis virescens larvae were fed a standard diet to which had been added E. coli cells harboring various plasmids and known to either have or not have the P-2 gene present. After seven days on the diet the larvae were scored for growth and viability with the results reported below in Table I. It is apparent from these results that the cloned P-2 gene is, in fact, expressed in E. coli, a non-sporulating bacteria, and that the product of the expression of this cloned gene renders the transformed E. coli significantly more toxic to Heliothis virescens larva than E. coli without the P-2 gene present.

TABLE I

| E. coli (plus Plasmid) | Dose | H. virescens larvae dead or stunted/total |
|---|---|---|
| Strain EG1303 (pBR322 no P-2 gene) | 10 mg/cup | 2/20 |
| Strain EG1304 (pEG201 P-2 gene present) | 10/mg/cup | 20/20 |

Example 2—Transformation of the P-2 Gene into Bacillus MEgaterium

Plasmid pEG201 (containing the P-2 gene) will replicate only in gram-negative strains such as E. coli. The P-2 gene was expressed in E. coli strain EG1304 harboring pEG201 but only at a low level (see Bioassay data, Table I). The purpose of this example was to determine whether the cloned P-2 gene would be expressed at a higher level in other Bacillus strains. In order to test for the expression of the cloned P-2 gene in a Bacillus strain it was first necessary to construct a recombinant plasmid that contained the P-2 gene and that was capable of replicating in Bacillus. A Bacillus-*E. coli* "shuttle vector" that contained the P-2 gene was constructed. The term "shuttle vector" indicates that the plasmid is capable of replication both in Bacillus and in *E. coli*. The *E. coli - Bacillus* shuttle vector was constructed by digestion of the Bacillus plasmid pBC16 (tetracycline resistance) with Sphl, ligation of the digested plasmid into the Sphl site of pEG201 (ampicillin resistance) and transformation of *E. coli* to ampicillin and tetracycline resistance.

One tet and amp resistant *E. coli* transformant harbored a plasmid (designated pEG204) that was composed of pBC16 inserted into the Sphl site of pEG201 (FIG.

FIG. 1 shows the restriction map of plasmid pEG204. The boxed areas denote plasmid vector DNA. The open box is pBR322 DNA (*E. coli* replication) and the cross-hatched box is pBC16 DNA (*Bacillus* replication). The horizontal line is cloned DNA from strain HD263-1. The large arrow denotes the coding region of the P-2 gene. pEG204 was transformed into *Bacillus megaterium* (NRRL accession Number B018203) and one tetracycline resistant transformant harboring pEG204 (designated strain EG1312) was chosen for further study.

This example determined if the cloned P-2 gene was expressed in the recombinant *B. megaterium* strain EG1312 (pEG204). Gene expression was measured by the technique of NadodeSO4/polyacrylamide gel electrophoresis. Generally, the technique involved preparation of cell lysates, electrophoresis of cell lysates through a NadodeSO4/polyacrylamide gel and staining of the gel to permit visualization of proteins.

Specifically, the technique was carried out as follows: *B. megaterium* cells were grown on DS plates containing 10 ug/ml tetracycline for 48 hr. at 30° C. *B. thuringiensis* strains were grown similarly to *B. megaterium* except the DS plates contained no tetracycline. After this period almost all cells had entered the stationary phase of growth. Cells were harvested with a spatula and resuspended in deioinized water. A portion of the cell suspension was mixed 1:2 vol:vol with preheated (70° C.) gel loading buffer (5% Beta -mercaptoethanol, 2% NaDodeSO4, 60 mM Tris pH 6.8, 10% glycerol) and incubated at 70° C. for 7 min. The suspension was centrifuged briefly, after centrifugation the supernatant was immediately loaded onto an NadodeSO4/polyacrylamide gel and the proteins in the supernatant were resolved by gel electrophoresis according to the method of Laemmli. (J. or Mol. Bio., 80:575-599 (1973)). The proteins in the gel were visualized by staining the gel with Coomassie dye.

FIG. 5 shows the results of this analysis. FIG. 5 is a photograph of an NadodeSO4/polyacrylamide gel that had been prepared as described above. This lane labeled STND in FIG. 5 contained protein molecular weight standards. Numbers to the right of the gel indicate protein sizes in kelodaltons (kDa). The lane labeled HD1-1 contained extracts of that B.t strain. The major protein band that corresponded to P-2 protein is indicated by an arrow. The lane labeled P2 contained a portion of the purified P-2 protein. The P2 protein was purified as described above.

The landes labeled EG1311 and EG1312 in FIG. 5 contained extracts of these *B. megaterium* strains harboring pBC16 and pEG204(P2) respectively. comparison of lanes EG1311 and EG1312 showed that extracts of strain EG1312(pEG204) contained a major protein that corresponded in size to that of the P2 protein. This protein was not present in extracts of strain EG1311(pBC16). This demonstrates that *B. megaterium* harboring the cloned P-2gene synthesized high levels of P2 protein. In addition, when viewed under the light microscope the cells of strain EG1312 appeared to contain phase-bright protein inclusion bodies characteristic of crystal toxins.

Bioassay of the Expression Product of the Cloned P-2 Gene in *B. Megaterium*

Standard toxicity tests carried out indicate that strain *Bacillus magaterium* EG1312 has an LD50 (5% of larvae dead) of 1.4 ug of bacterial cells per insect food cup when fed to either *Heliothis virescens* (H.v.) or to *Lymantria dispar* (L.d.) larvae. In contrast the control strain of *Bacillus megaterium* harboring the plasmid vector pBC16 without the P-2gene failed to skill either H.v. or L.d. larvae at a dose of 10 ug bacterial cells per food cup.

*B. megaterium* strain EG1312 (EG204-P2) was also tested for toxicity against *A. aegypti*. A cell suspension was prepared by growing strains EG1311(pBC16-negative control) and EG1312 on solid DS medium containing 10 ug/ml tetracycline for 45 hr. at 30° C. Cells were harvested with a spatula and cells were resuspended in deionized water. Serial dilutions of the cell suspension were made. Twenty larvae (third or fourth instar) of *A. aegypti* were placed in 100 ml of the cell suspensions and mortality was scored after 48 hr. The results (below) showed that strain EG1312(P2) is toxic to mosquito larvae. In contrast *B. megaterium* containing the vector plasmid PBC16 alone (strain EG1311) was not toxic to mosquito larvae.

TABLE II

| Dose-mg cells/ml | *A. aegypti* larvae # dead/total |
|---|---|
| EG1311 (pBC16 control)-0.8 mg/ml | 0/20 |
| EG1312 (pEG204-P2) | |
| 0.8 mg/ml | 10/20 |
| 0.4 mg/ml | 12/20 |
| 0.2 mg/ml | 10/20 |
| 0.1 mg/ml | 9/20 |
| EG1311 (control)-0.9 mg/ml | 0/20 |
| EG1312 (pEG204-P2) | |
| 0.9 mg/ml | 16/20 |
| 0.8 mg/ml | 16/20 |
| 0.4 mg/ml | 15/20 |
| 0.2 mg/ml | 12/20 |
| 0.1 mg/ml | 12/20 |

DEPOSIT OF MICROORGANISMS

It is within the scope of this invention that a wide variety of both sporulating and nonsporulating microorganism may be transformed with the P-2 as described herein. Exemplary of the microorganisms which may be engineered as taught herein are those from the genera *Bacillus, Escherichia*, and *Cyanobacteria*. Preferred for use with this invention are the organisms *Bacillus megaterium* and *Escherichia coli*. In addition, the following *Bacillus thuringiensis, Bacillus megaterium* and *E.* coli strains which are also preferred for use with this invention and which carrying the listed plasmids have been deposited with the Agricultural Research Culture Collection (NRRL), Peoria, IL and have been assigned the listed accession numbers:

|  | Plasmids | Accession Numbers |
|---|---|---|
| B. thuringiensis strain |  |  |
| HD1-1 | Several naturally occuring | B-18201 |
| HD263-1 | Several naturally occuring | B-18202 |
| B. megaterium |  |  |
| EG1312 | pEG204 | B-18203 |
| E. coli |  |  |
| EG1304 | pEG201 | B-18204 |

The present invention is not to be limited in scope by this microorganism deposited, since the deposited embodiment is intended as a single illustration of one aspect of the invention. Indeed, various modifications of the invention in addition to those shown and described herein will become apparent to those skilled in the art from the foregoing description and accompanying drawings.

I claim:

1. A purified and isolated gene for Bacillus thuringiensis P2 toxin having the DNA sequence of FIG. 2.

2. The gene of claim 1 wherein said gene codes for a protein having the amino acid sequence of FIG. 2.

3. The gene of claim 2 wherein said protein has insecticidal activity.

4. The gene of claim 3 wherein said insecticidal activity is effective against insects selected from the orders consisting of lepidoptera and diptera.

5. The gene of claim 1 wherein said DNA sequence is inserted into a recombinant plasmid.

6. The gene of claim 5 wherein said plasmid is comprised of DNA from at least two different species of microorganisms after insertion of said DNA sequence.

7. The gene of claim 1 wherein said plasmid is comprised of DNA from at least two different subspecies of the same species of microorganism after insertion of said DNA sequence.

8. The gene of claim 1 wherein said DNA sequence is attached to its native promoter DNA sequence.

9. The gene of claim 1 wherein said DNA sequence is attached to a foreign promoter DNA sequence.

10. A recombinant vecotr containing the DNA sequence of claim 1.

11. The DNA sequence of FIG. 2 wherein the DNA or a portion or derivative thereof is labeled for use as a P-2 hybridization probe.

12. The DNA sequence of claim 11 wherein the DNA or a portion of derivative thereof is labeled with a radioactive label.

* * * * *